US011224354B2

(12) United States Patent
Añó

(10) Patent No.: US 11,224,354 B2
(45) Date of Patent: Jan. 18, 2022

(54) SYSTEMS AND METHODS OF MONITORING ELECTRODERMAL ACTIVITY (EDA) USING AN AC SIGNAL AND DISCRETE FOURIER TRANSFORM (DFT) ANALYSIS

(71) Applicant: Analog Devices International Unlimited Company, Limerick (IE)

(72) Inventor: José Carlos Conchell Añó, Alfarp (ES)

(73) Assignee: ANALOG DEVICES INTERNATIONAL UNLIMITED COMPANY

( * ) Notice: Subject to any disclaimer, the term of this patent is extended or adjusted under 35 U.S.C. 154(b) by 834 days.

(21) Appl. No.: 15/230,637

(22) Filed: Aug. 8, 2016

(65) Prior Publication Data

US 2018/0035910 A1    Feb. 8, 2018

(51) Int. Cl.
    *A61B 5/0531* (2021.01)
    *A61B 5/00* (2006.01)

(52) U.S. Cl.
    CPC .......... *A61B 5/0531* (2013.01); *A61B 5/7257* (2013.01); *A61B 2562/0209* (2013.01)

(58) Field of Classification Search
    CPC .................................................. A61B 5/0531
    See application file for complete search history.

(56) References Cited

U.S. PATENT DOCUMENTS

| 5,427,113 A * | 6/1995 | Hiroshi | A61B 5/0531 |
| | | | 600/547 |
| 2003/0006782 A1 * | 1/2003 | Shambroom | A61B 5/0476 |
| | | | 324/614 |

(Continued)

FOREIGN PATENT DOCUMENTS

| EP | 1 437 091 A1 | 10/2003 |
| WO | WO 2014/147024 A1 | 9/2014 |

OTHER PUBLICATIONS

Wolfram Boucsein, University of Wuppertal, "Electrodermal Activity", Second Edition, Springer Science+Business Media, LLC 2012, pp. 96-98, 130-133.

(Continued)

*Primary Examiner* — Daniel L Cerioni
*Assistant Examiner* — Yasmeen S Warsi
(74) *Attorney, Agent, or Firm* — Patent Capital Group

(57) ABSTRACT

Systems and methods of monitoring electrodermal activity (EDA) in human subjects suitable for use in wearable electronic devices. An EDA monitoring system can include first and second dry electrodes, an alternating current (AC) excitation signal source, a trans-impedance amplifier, an analog-to-digital (A-to-D) converter, a discrete Fourier transform (DFT) processor, and a microprocessor. The AC excitation signal source can produce an AC excitation signal having a predetermined excitation frequency, such as about 100 or 120 Hertz (Hz). The analog-to-digital (A-to-D) converter can include a sample-and-hold circuit that operates at a predetermined sampling frequency, such as about four times (4×) the predetermined excitation frequency of 100 or 120 Hz. The DFT processor can generate complex frequency domain representations of digitized, sampled voltage level sequences provided by the A-to-D converter for use in obtaining measures of a user's skin impedance or skin conductance.

22 Claims, 7 Drawing Sheets

(56) References Cited

U.S. PATENT DOCUMENTS

| | | | |
|---|---|---|---|
| 2006/0034493 A1* | 2/2006 | Shimamura | A61B 5/1172 |
| | | | 382/115 |
| 2009/0264792 A1* | 10/2009 | Mazar | A61B 5/0531 |
| | | | 600/547 |
| 2010/0179403 A1 | 7/2010 | Martinsen et al. | |
| 2013/0231547 A1 | 9/2013 | Kim et al. | |
| 2014/0316229 A1* | 10/2014 | Tognetti | A61B 5/0533 |
| | | | 600/383 |
| 2014/0323826 A1* | 10/2014 | Wilder-Smith | A61B 5/01 |
| | | | 600/301 |
| 2014/0378859 A1 | 12/2014 | Taratorin et al. | |
| 2015/0359452 A1* | 12/2015 | Giovangrandi | A61B 5/0295 |
| | | | 600/547 |
| 2016/0128577 A1 | 5/2016 | Campbell et al. | |

OTHER PUBLICATIONS

IOP Publishing, Physiological Measurement, "Electrical measurement of sweat activity", Physiol. Meas. 29(2008), pp. 407-415.

* cited by examiner

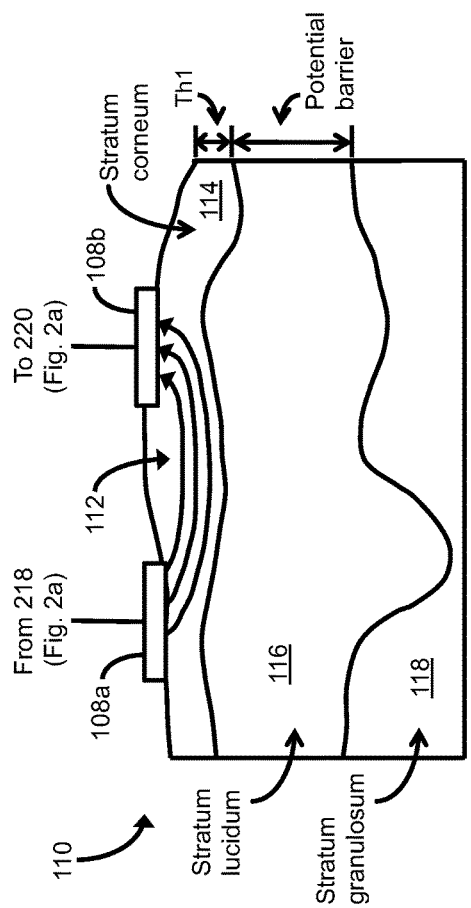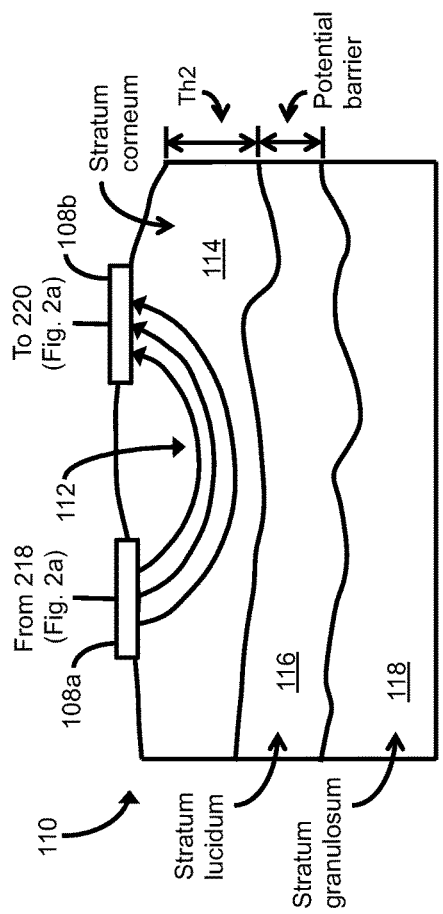

SYSTEMS AND METHODS OF MONITORING ELECTRODERMAL ACTIVITY (EDA) USING AN AC SIGNAL AND DISCRETE FOURIER TRANSFORM (DFT) ANALYSIS

FIELD OF THE DISCLOSURE

The present application relates generally to systems and methods of monitoring electrodermal activity (EDA) in human subjects, and more specifically to systems and methods of monitoring EDA that are suitable for use in wearable electronic devices.

BACKGROUND

In recent years, activity trackers and other wearable electronic devices have gained increased popularity due to users' desire to monitor, measure, and/or track, in real-time, various aspects relating to their fitness and/or health, including, but not limited to, the number of steps taken by a user, the user's heart rate and/or heart rate variability, the user's temperature, the user's activity and/or stress levels, etc. One known technique for determining a user's activity and/or stress levels involves monitoring, measuring, and/or tracking the electrodermal activity (EDA) of the user's skin, which can be performed by measuring the skin impedance or skin conductance. For example, in response to an environmental, psychological, and/or physiological arousal, the user's skin perspiration may increase as the thickness of the stratum corneum (i.e., the outer layer of the user's skin) decreases, thereby causing a decrease the skin impedance or an increase in the skin conductance. By measuring changes in the skin impedance or the skin conductance over time, metrics can be obtained relating to the user's activity level, stress level, pain level, and/or other factor(s) associated with the user's present psychological and/or physiological condition, allowing the user to take appropriate steps to address the condition based on the obtained metrics, as necessary.

A conventional wearable electronic device for measuring the EDA of a user's skin includes a first electrode for contacting a first area of the user's skin, a second electrode for contacting a second area of the user's skin, an excitation signal source, a trans-impedance amplifier, an instrumentation amplifier, an analog-to-digital (A-to-D) converter, and a processing module. The first and second electrodes can each be a dry electrode or a wet electrode. The excitation signal source can be a direct current (DC) signal source or an alternating current (AC) signal source. For example, such a conventional wearable electronic device for measuring EDA of a user's skin may be implemented in a wristband, a headband, an armband, a foot band, an ankle band, or one or more finger rings. In one mode of operation, the excitation signal source can generate a DC or AC signal, causing a DC or AC current to flow through the stratum corneum of the user's skin from the first electrode contacting the first area of the user's skin to the second electrode contacting the second area of the user's skin. The trans-impedance amplifier can convert the DC or AC current received at the second electrode to a DC or AC voltage, respectively, and the instrumentation amplifier can obtain the DC or AC voltage difference across the first and second electrodes. The A-to-D converter can convert each of the DC or AC voltage from the trans-impedance amplifier and the DC or AC voltage difference from the instrumentation amplifier from analog form to digital form, and provide the DC or AC voltage and DC or AC voltage difference in their digital forms to the processing module. The processing module can analyze such DC or AC voltages and voltage differences to obtain absolute measures of the user's skin impedance or skin conductance. If the skin impedance is found to have decreased (or the skin conductance is found to have increased) over time, then the user's activity level, stress level, emotional state, and/or pain level, etc., can be deemed to have increased. If the skin impedance is found to have increased (or the skin conductance is found to have decreased) over time, then the user's activity level, stress level, emotional state, and/or pain level, etc., can be deemed to have decreased.

SUMMARY OF THE DISCLOSURE

In accordance with the present application, systems and methods of monitoring electrodermal activity (EDA) in human subjects are disclosed that are suitable for use in wearable electronic devices. In certain embodiments, an exemplary EDA monitoring system can include a first dry electrode for contacting a first area of a user's skin, a second dry electrode for contacting a second area of the user's skin, and an alternating current (AC) excitation signal source for producing an AC excitation signal having a predetermined excitation frequency, such as about 100 Hertz (Hz) or 120 Hz. The AC excitation signal can cause an AC current to flow through the stratum corneum (i.e., the outer layer of the user's skin) from the first dry electrode contacting the first area of the user's skin to the second dry electrode contacting the second area of the user's skin. The EDA monitoring system can further include (1) a trans-impedance amplifier for converting the AC current received at the second dry electrode to an AC voltage, (2) an analog-to-digital (A-to-D) converter for sampling the AC voltage at a predetermined sampling frequency, such as about four times (4×) the predetermined excitation frequency, in order to obtain a voltage level sequence, and for converting the voltage level sequence from analog form to digital form, (3) a discrete Fourier transform (DFT) processor for generating a complex frequency domain representation of the sampled voltage level sequence, and (4) a microprocessor or any other suitable integrated circuitry for processing and analyzing the representation of the sampled voltage level sequence in the complex frequency domain in order to obtain relative measures of the user's skin impedance or skin conductance. By sampling the AC voltage at the predetermined sampling frequency of about four times (4×) the predetermined excitation frequency of 100 Hz or 120 Hz, and generating a representation of the sampled voltage level sequence in the complex frequency domain, the EDA monitoring system can advantageously obtain relative measures of the user's skin impedance or skin conductance with reduced electrolysis of the first and second electrodes, reduced computational complexity, and increased signal-to-noise ratio (SNR). Moreover, by obtaining relative measures of the user's skin impedance or skin conductance, both the structural complexity and the cost of the EDA monitoring system can advantageously be reduced. Such an EDA monitoring system is particularly suited for use in wearable electronic devices configured as wristbands, headbands, armbands, foot bands, ankle bands, or finger rings.

In certain further embodiments, a system for monitoring electrodermal activity can include a first dry electrode for making contact with a first area of skin, a second dry electrode for making contact with a second area of the skin, and an excitation channel operative to provide an AC excitation signal at a predetermined excitation frequency, thereby causing an AC current to flow between the first dry electrode and the second dry electrode through a stratum corneum of the skin. The system can further include a reception channel including a trans-impedance amplifier and an A-to-D converter. The trans-impedance amplifier is operative to convert the AC current to an AC voltage signal. The A-to-D converter is operative to sample the AC voltage signal at a sampling frequency of four times (4×) the predetermined excitation frequency, and to convert the sampled AC voltage signal to a digitized voltage level sequence. The system can still further include a DFT processor operative to generate a complex frequency domain representation of the digitized voltage level sequence.

In still further embodiments, a method of monitoring electrodermal activity can include providing an AC excitation signal at a predetermined excitation frequency to cause an AC current to flow between a first dry electrode and a second dry electrode through a stratum corneum of skin. The first dry electrode can make contact with a first area of the skin, and the second dry electrode can make contact with a second area of the skin. The method can further include converting the AC current to an AC voltage signal, sampling the AC voltage signal at a sampling frequency of four times (4×) the predetermined excitation frequency, converting the sampled AC voltage signal to a digitized voltage level sequence, and performing a DFT to generate a complex frequency domain representation of the digitized voltage level sequence.

In yet further embodiments, a system for monitoring electrodermal activity can include a first dry electrode for making contact with a first area of skin, a second dry electrode for making contact with a second area of skin, and an excitation signal source operative to generate a square wave signal at a predetermined excitation frequency. The system can further include a level shifter operative to level-shift the square wave signal, and a low-pass filter operative to convert the level-shifted square wave signal to an AC sinusoidal signal, and to apply the AC sinusoidal signal to a first capacitor connected to the first dry electrode, thereby causing an AC current to flow between the first dry electrode and the second dry electrode through a stratum corneum of the skin. The system can still further include a trans-impedance amplifier operative to receive the AC current through a second capacitor connected to the second dry electrode, and to convert the AC current to an AC voltage signal. The system can yet further include an A-to-D converter operative to sample the AC voltage signal at a sampling frequency of four times (4×) the predetermined excitation frequency, and to convert the sampled AC voltage signal to a digitized voltage level sequence. The system can still yet further include a DFT processor operative to generate a complex frequency domain representation of the digitized voltage level sequence, as well as integrated circuitry operative to obtain a relative measure of skin impedance or skin conductance based on the digitized voltage level sequence.

Other features, functions, and aspects of the invention will be evident from the Detailed Description that follows.

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings:

FIG. 1a is a diagram of a cross-section of the skin of an exemplary human subject, illustrating the stratum corneum (i.e., the outer layer of the user's skin) having a first thickness and a corresponding first skin impedance or skin conductance;

FIG. 1b is a diagram of a further cross-section of the skin of the human subject of FIG. 1a, illustrating the stratum corneum having a second thickness and a corresponding second skin impedance or skin conductance;

FIG. 2b is a block diagram of an analog-to-digital (A-to-D) converter included in the system of FIG. 2a;

FIG. 5 is a flow diagram of an exemplary method of monitoring the EDA in a human subject, using the system of FIG. 2a.

DETAILED DESCRIPTION

Figure 1C:
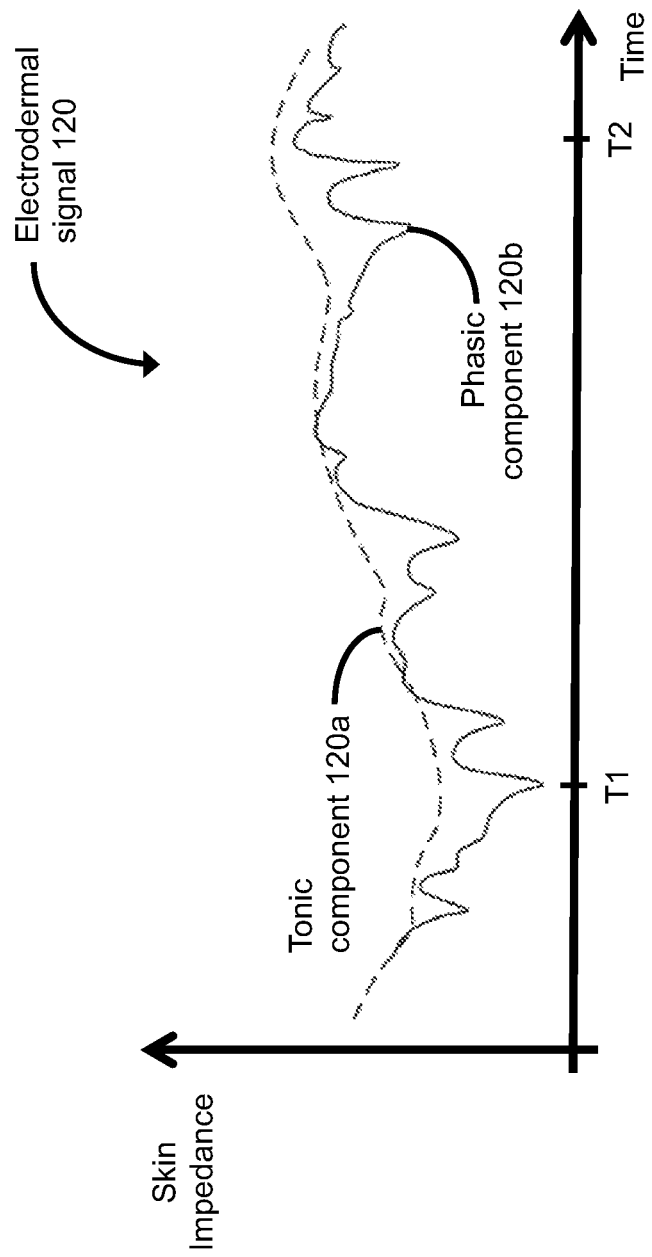
FIG. 1c is a diagram of an exemplary electrodermal signal representative of electrodermal activity (EDA) in the skin of the human subject of FIGS. 1a and 1b.

Systems and methods of monitoring electrodermal activity (EDA) in human subjects are disclosed that are suitable for use in wearable electronic devices. In one embodiment, an EDA monitoring system is disclosed that can include first and second dry electrodes, an alternating current (AC) excitation signal source, a trans-impedance amplifier, an analog-to-digital (A-to-D) converter, a discrete Fourier transform (DFT) processor, and a microprocessor. The AC excitation signal source can produce an AC excitation signal having a predetermined excitation frequency, such as about 100 Hertz (Hz) or 120 Hz. The analog-to-digital (A-to-D) converter can include a sample-and-hold circuit that operates at a predetermined sampling frequency, such as about four times (4×) the predetermined excitation frequency of 100 Hz or 120 Hz. The DFT processor can generate complex frequency domain representations of one or more digitized, sampled voltage level sequences provided by the A-to-D converter for use in obtaining relative measures of a user's skin impedance or skin conductance.

The disclosed EDA monitoring systems and methods can avoid at least some of the drawbacks of conventional EDA monitoring systems and methods, particularly those that are targeted for use in wearable electronic devices. For example, such conventional EDA monitoring systems and methods often employ so-called "dry" electrodes in conjunction with direct current (DC) excitation signals. Such dry electrodes can be distinguished from so-called "wet" electrodes, which typically require the application of a conductive gel or liquid between each wet electrode and the user's skin for proper operation, and are therefore generally inconvenient and impractical for use in wearable electronic devices. However, employing dry electrodes (e.g., silver (Ag) electrodes) and DC excitation signals in such conventional EDA monitoring systems may result in electrolysis of the dry electrodes during use, which may lead to corrosion of the dry electrodes over time and/or skin irritation due to the deposit of Ag ions (i.e., $Ag^+ + e^-$). Such conventional EDA monitoring systems and methods are also often subjected to environmental noise signals (e.g., 50 or 60 Hz power line noise) and/or noise signals from internal electronics of the wearable electronic devices, which can have adverse effects upon skin impedance or skin conductance measurements. Such conventional EDA monitoring systems typically employ band-pass filtering elements in an effort to mitigate the adverse effects of such noise signals. However, such added filtering elements may contribute to increased complexity and/or cost of the wearable electronic devices.

In order to avoid at least some of the drawbacks of conventional EDA monitoring systems and methods, the disclosed EDA monitoring system employs dry electrodes in conjunction with AC excitation signals, which typically cause little or no electrolysis of the dry electrodes during use. Further, the sample-and-hold circuit included in the A-to-D converter of the disclosed EDA monitoring system operates at a sampling frequency of about 4× the excitation frequency of 100 Hz or 120 Hz, allowing the DFT processor to generate complex frequency domain representations of the resulting digitized, sampled voltage level sequences with reduced computational complexity. In addition, by processing and analyzing the representations of the digitized, sampled voltage level sequences in the complex frequency domain, the microprocessor or any other suitable integrated circuitry can separate unwanted noise from the sampled voltage level information to obtain more accurate measures of the user's skin impedance or skin conductance. Moreover, by obtaining relative measures of the user's skin impedance or skin conductance, both the structural complexity and the cost of the disclosed EDA monitoring system can advantageously be reduced.

FIGS. 1a and 1b depict the cross-section of skin 110 of an exemplary human subject, showing a stratum corneum 114 (i.e., the outer layer of the skin 110), the stratum granulosum 118, and the stratum lucidum 116 disposed between the stratum corneum 114 and the stratum granulosum 118. As shown in FIG. 1a, the stratum corneum 114 can have an exemplary first thickness Th1 spanning from the upper surface of the skin 110 to a potential barrier between the stratum corneum 114 and the stratum lucidum 116. As shown in FIG. 1b, the stratum corneum 114 can also have at least an exemplary second thickness Th2 spanning from the upper surface of the skin 110 to the potential barrier between the stratum corneum 114 and the stratum lucidum 116. The thickness (e.g., Th1, Th2) of the stratum corneum 114 can change based on the human subject's present psychological and/or physiological condition. For example, in response to an environmental, psychological, and/or physiological arousal of the human subject, the human subject's skin perspiration may increase as the thickness of the stratum corneum 114 decreases (see, e.g., the thickness Th1 of FIG. 1a), thereby causing a decrease the skin impedance or an increase in the skin conductance. Further, as the human subject achieves a level of relaxation, the human subject's skin perspiration may decrease as the thickness of the stratum corneum 114 increases (see, e.g., the thickness Th2 of FIG. 1b), thereby causing an increase the skin impedance or a decrease in the skin conductance.

In order to obtain a measure of the human subject's skin impedance or skin conductance, a first dry electrode 108a and a second dry electrode 108b can be placed in contact with a first area and a second area, respectively, of the human subject's skin 110, such that the distance between the first and second dry electrodes 108a, 108b is greater than the thickness Th1 or Th2 of the stratum corneum 114. Further, an excitation signal source 216 (see FIG. 2a) can generate an AC signal, causing an AC current 112 to flow through the stratum corneum 114 from the first dry electrode 108a contacting the first area of the human subject's skin 110 to the second dry electrode 108b contacting the second area of the human subject's skin 110. The AC current 112 received at the second dry electrode 108b can then be processed to obtain an electrodermal signal, which can be analyzed to obtain a measure of the human subject's skin impedance or skin conductance. For example, the first dry electrode 108a and the second dry electrode 108b may each be a silver (Ag) electrode, or any other suitable electrode.

FIG. 1c depicts an exemplary electrodermal signal 120, which may be obtained in response to the flow of the AC current 112 through the stratum corneum 114 of the skin 110 of the exemplary human subject. As shown in FIG. 1c, the electrodermal signal 120 includes a low frequency tonic component 120a and a higher frequency phasic component 120b. In the electrodermal signal 120 of FIG. 1c, the tonic component 120a generally corresponds to the skin impedance of the human subject in the absence of an environmental, psychological, and/or physiological arousal, and the phasic component 120b generally corresponds to the skin impedance of the human subject in response to such an environmental, psychological, and/or physiological arousal, which can involve sight, sound, scent, touch, pain, stress, cognitive processes involving anticipation, decision making, etc. For example, the electrodermal signal 120 may provide a measure of skin impedance at the wrist of the human subject, the absolute value of which can range from about 20,000 Ohms at time T1 to about 20,000,000 Ohms at time T2. Further, the skin impedance at time T1 may correspond to the exemplary thickness Th1 of the stratum corneum 114 depicted in FIG. 1a, and the skin impedance at time T2 may correspond to the exemplary thickness Th2 of the stratum corneum 114 depicted in FIG. 1b. It is noted that the corresponding absolute value of skin conductance at the wrist of the human subject can range from about 50 micro-Siemens (µS) to about 0.05 µS.

Figure 2A:
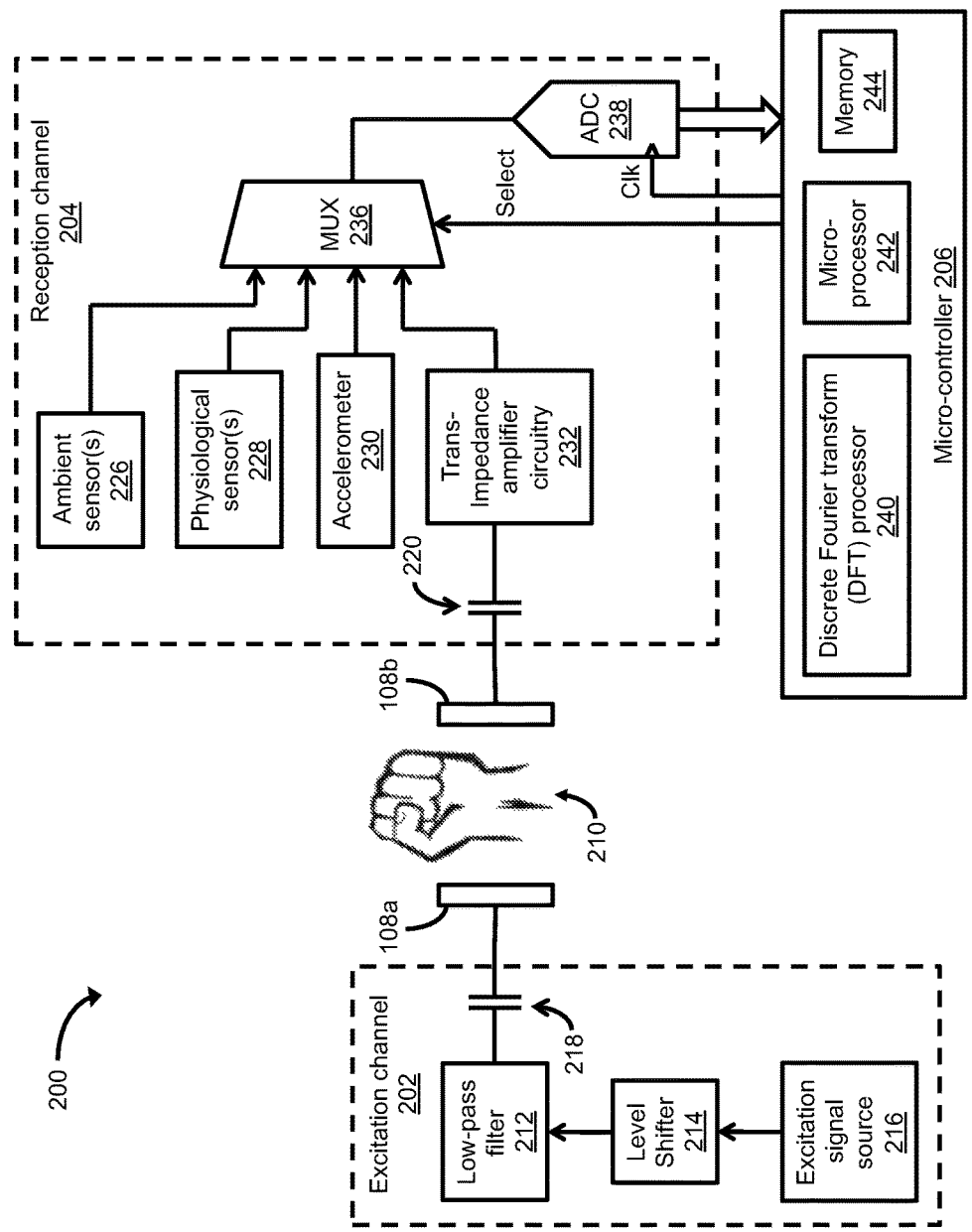
FIG. 2a is a block diagram of an exemplary system for monitoring EDA in a human subject, according to the present application.

FIG. 2a depicts an illustrative embodiment of an exemplary system 200 for monitoring EDA (also referred to herein as the "EDA monitoring system") in a human subject, in accordance with the present application. As shown in FIG. 2a, the EDA monitoring system 200 includes an excitation channel 202, a reception channel 204, the first and second dry electrodes 108a, 108b, and a micro-controller 206. The excitation channel 202 can include an excitation signal source 216, a level shifter 214, a low-pass filter 212, and a capacitor 218. The reception channel 204 can include one or more ambient sensors 226, one or more physiological sensors 228, an accelerometer 230, a capacitor 220, trans-impedance amplifier circuitry 232, a multiplexor (MUX) 236, and an analog-to-digital (A-to-D) converter 238. The micro-controller 206 can include a discrete Fourier transform (DFT) processor 240, a microprocessor 242, and a memory 244. For example, the EDA monitoring system 200 may be implemented in a wearable electronic device configured as a wristband, a headband, an armband, a foot band, an ankle band, one or more finger rings, or any other suitable wearable electronic device.

Figure 4:
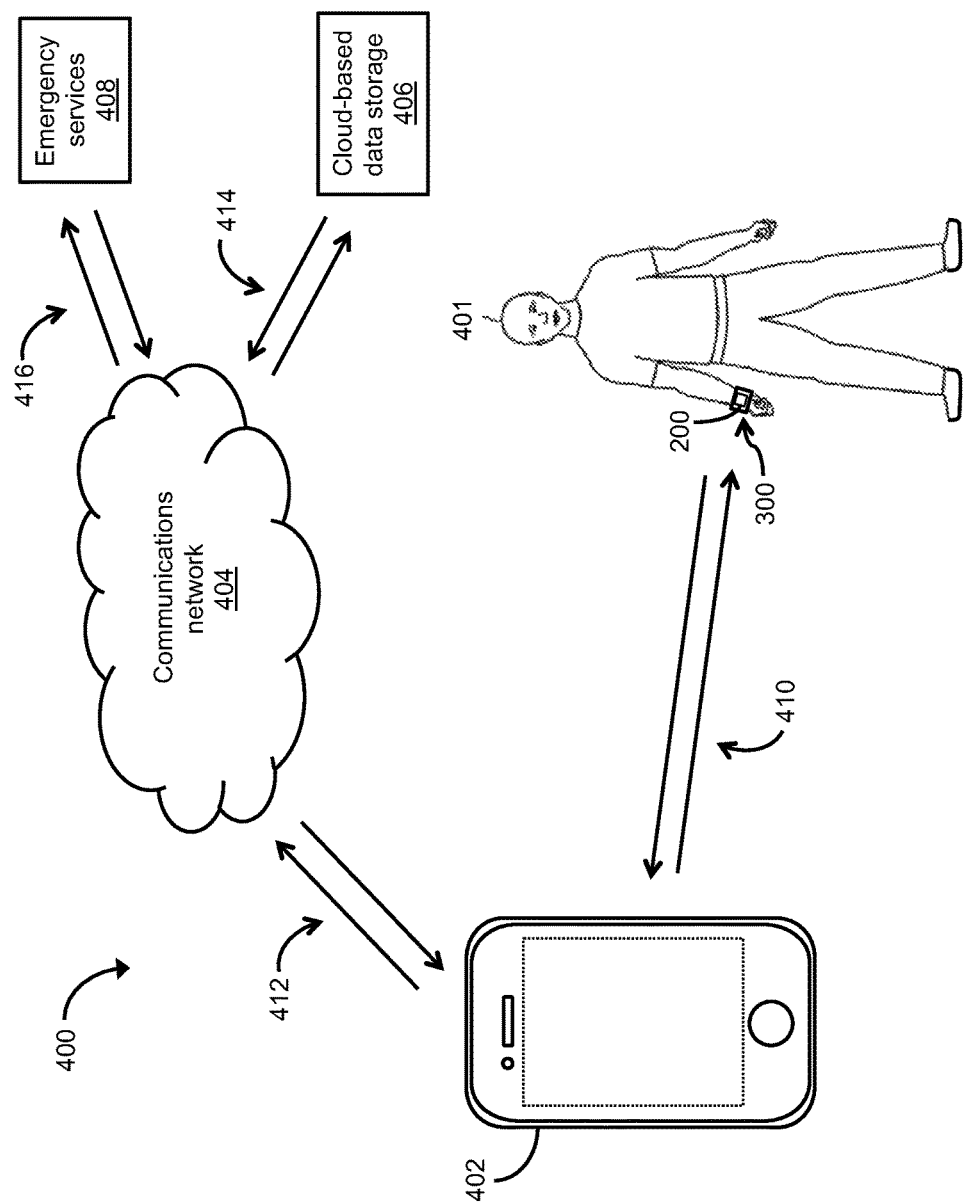
FIG. 4 is a diagram illustrating an exemplary environment in which the system of FIG. 2a may be employed.
Figure 5:
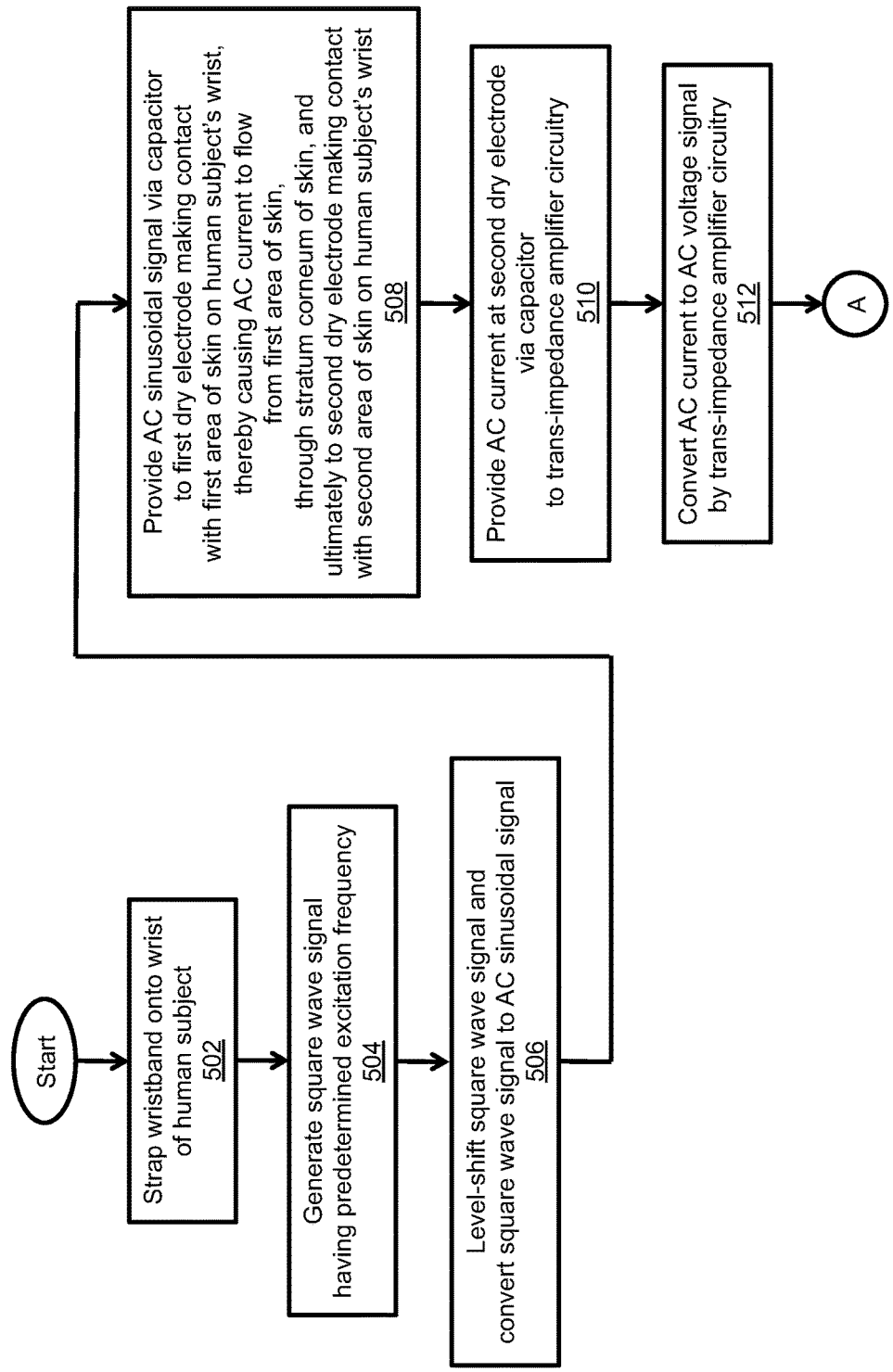
Figure 5:
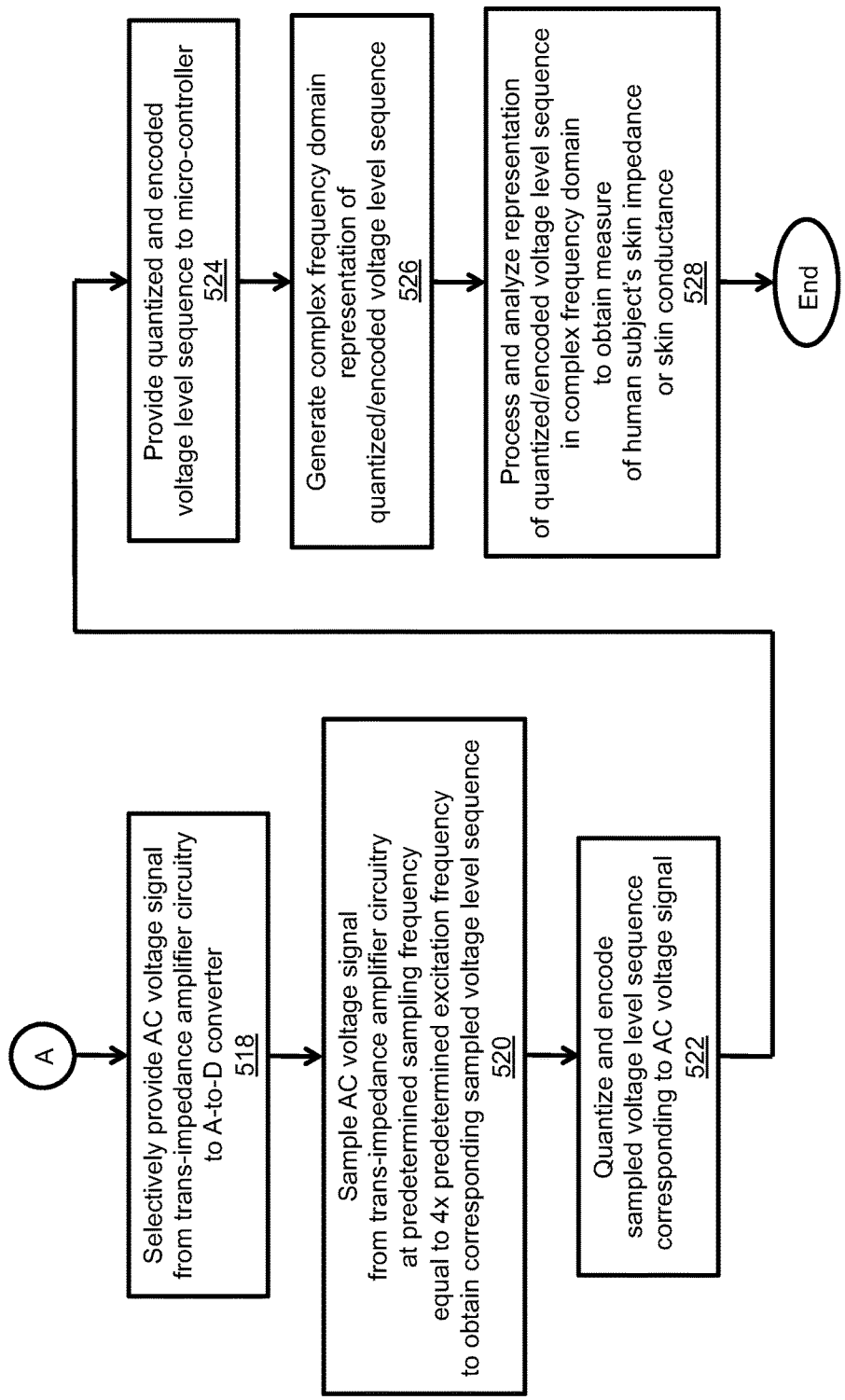

In an exemplary mode of operation, the EDA monitoring system 200 (see FIG. 2a) can be implemented in a wearable electronic device configured as a wristband, which may be worn on a wrist 210 of a human subject (such as the human subject 401; see FIG. 4). In this exemplary mode of operation, the excitation signal source 216 can generate a 100 Hz or 120 Hz square wave signal. Such a square wave signal can be level-shifted by the level shifter 214 to mitigate ground noise before being converted to an AC sinusoidal signal by the low-pass filter 212, which can be a $2^{nd}$ order low-pass filter or any other suitable filter. The capacitor 218 included in the excitation channel 202, as well as the capacitor 220 included in the reception channel 204, can provide capacitive isolation for the wrist 210 of the human subject. The AC sinusoidal signal is provided via the capacitor 218 to the first dry electrode 108a, which can be in contact with a first area of skin on the human subject's wrist 210. The AC sinusoidal signal at the first dry electrode 108a can cause an AC current to flow from the first area of skin on the human subject's wrist 210, through the stratum corneum of the skin, and ultimately to the second dry electrode 108b, which can be in contact with a second area of skin on the human subject's wrist 210. The AC current at the second dry electrode 108b is provided via the capacitor 220 to the trans-impedance amplifier circuitry 232, which can convert the AC current to an AC voltage signal. The MUX 236 can selectively provide, under control of the micro-controller 206, the AC voltage signal from the trans-impedance amplifier circuitry 232 to the A-to-D converter (ADC) 238.

Figure 2B:
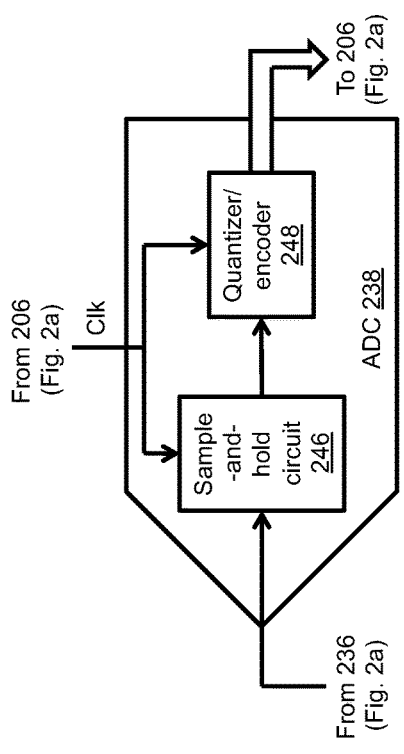

FIG. 2b depicts a detailed view of the A-to-D converter (ADC) 238. As shown in FIG. 2b, the A-to-D converter (ADC) 238 can include a sample-and-hold circuit 246 and a quantizer/encoder 248. Each of the sample-and-hold circuit 246 and the quantizer/encoder 248 can receive a clock (CLK) signal from the micro-controller 206. In this exemplary mode of operation, the sample-and-hold circuit 246 can sample the AC voltage signal from the trans-impedance amplifier circuitry 232 at a predetermined sampling frequency, such as about four times (4×) the frequency (e.g., 100 Hz or 120 Hz) of the square wave (also referred to herein as the "excitation frequency") generated by the excitation signal source 216. Having sampled the AC voltage signal at the predetermined sampling frequency, the sample-and-hold circuit 246 can provide a corresponding sampled voltage level sequence to the quantizer/encoder 248, which can quantize and encode the sampled voltage level sequence in order to provide a corresponding digitized, sampled voltage level sequence (e.g., a sequence of binary encoded numbers) to the micro-controller 206.

As described herein, the skin impedance or the skin conductance of a human subject can change based on the human subject's present psychological and/or physiological condition. In order to better track certain factors that can affect the human subject's psychological and/or physiological condition, the reception channel 204 can include the ambient sensor(s) 226, the physiological sensor(s) 228, and the accelerometer 230. For example, the ambient sensor(s) 226 may include one or more sensors for gathering environmental data relating to the external temperature and/or humidity, and the physiological sensors 228 may include one or more sensors for gathering physiological data relating to the human subject's heart rate, heart rate variability, temperature, autonomous nervous system activity, and/or any other suitable physiological condition(s). Further, the accelerometer 230 may gather acceleration data relating to the human subject's motion, such as the number of steps taken by the human subject over a specified time period, or any other suitable motion of the human subject. The ambient sensor(s) 226, the physiological sensor(s) 228, and the accelerometer 230 can provide the environmental data, the physiological data, and the motion data to the MUX 236, which can selectively provide, under control of the micro-controller 206, the environmental, physiological, and/or motion data to the A-to-D converter 238. The A-to-D converter 238 can convert the environmental, physiological, and/or motion data from analog form to digital form, and provide the environmental, physiological, and/or motion data in their digital forms to the micro-controller 206 for processing, analysis, and/or storage in the memory 244.

Having received one or more digitized, sampled voltage level sequences corresponding to the AC voltage signal provided by the trans-impedance amplifier circuitry 232 at the micro-controller 206, the DFT processor 240 can generate one or more complex frequency domain representations of the respective sampled voltage level sequences. As described herein, the sample-and-hold circuit 246 can sample the AC voltage signal at the predetermined sampling frequency of about 4× the excitation frequency. By sampling the AC voltage signal at 4× the excitation frequency, the DFT processor 240 can generate the complex frequency domain representations of the respective sampled voltage level sequences with reduced computational complexity.

For example, the general expression for the discrete Fourier transform (DFT) may be formulated, as follows:

$$X(k) = \sum_{n=0}^{N-1} x(n) \cdot W_N^{nk} \quad (1)$$

in which $$W_N^{nk} = e^{-j2\pi nk/N} \quad (2)$$

and "k" is a non-negative integer ranging from 0 to N−1.

By employing a sampling frequency that is 4× the excitation frequency (e.g., 100 Hz or 120 Hz), the general expression for the DFT can be reduced, as follows:

$$X(\hat{k}) = \sum_{n=0}^{\frac{N}{4}-1} [x(4n) - x(4n+2)] + j \sum_{n=0}^{\frac{N}{4}-1} [x(4n+3) - x(4n+1)] \quad (3)$$

in which $$\hat{k} = 0, 1, \ldots, \frac{N}{4} - 1. \quad (4)$$

As shown in equation (3) above, the real and imaginary parts of the reduced DFT expression each include two (N/4)-point subsequences, namely, the two (N/4)-point subsequences "x(4n)" and "x(4n+2)" in the real part of the reduced DFT expression, and the two (N/4)-point subsequences "x(4n+3)" and "x(4n+1)" in the imaginary part of the reduced DFT expression. As a result, the real and imaginary parts of the reduced DFT expression (see equation (3)) can each be evaluated using basic arithmetic operations of addition and/or subtraction, thereby reducing the computational overhead and complexity of the DFT processor 240.

For example, in certain embodiments, the DFT processor 240 may evaluate the real ("real") and imaginary ("imag") parts of the reduced DFT expression (see equation (3)) by executing computer code in the C/C++ language (or any other suitable computer language), such as the following exemplary computer code:

```
For(uint8_t i=0; i<(NSAMPLES/4);i++)
{
    real=real+(int32_t)auxp[4*i]-(int32_t)auxp[(4*i)+2];
    imag=imag+(int32_t)auxp[(4*i)+3]-(int32_t)auxp[(4*i)+1];
}
```

As indicated in the exemplary computer code above, the evaluation of the real ("real") and imaginary ("imag") parts of the reduced DFT expression (see equation (3)) involves arithmetic operations of addition and/or subtraction, and avoids more computationally intensive arithmetic operations such as multiplication and/or division.

Having obtained, in accordance with equations (3) and (4) above, complex frequency domain representations of the sampled voltage level sequences corresponding to the AC voltage signal provided by the trans-impedance amplifier circuitry 232, the microprocessor 242 can process and analyze the representations of the sampled voltage level sequences in the complex frequency domain in order to obtain measures of the human subject's skin impedance or skin conductance. For example, the microprocessor 242 may obtain the magnitude, |ZsmN|, of the human subject's skin impedance in the complex frequency domain, as follows:

$$|Z_{SKIN}|=|APPLIED\_AC\_VOLTAGE|/|OBTAINED\_AC\_VOLTAGE|, \quad (5)$$

in which "|APPLIED_AC_VOLTAGE|" is the magnitude of a complex frequency domain representation of the known voltage of the AC sinusoidal signal applied to the skin on the human subject's wrist 210, and "|OBTAINED_AC_VOLTAGE|" is the magnitude of the complex frequency domain representation of the AC voltage signal obtained by the trans-impedance amplifier circuitry 232. Further, the microprocessor 242 may obtain the phase, Phase($Z_{SKIN}$), of the human subject's skin impedance in the complex frequency domain, as follows:

$$Phase(Z_{SKIN})=180+(Phase(APPLIED\_AC\_VOLTAGE)-Phase(OBTAINED\_AC\_VOLTAGE)), \quad (6)$$

in which "Phase(APPLIED_AC_VOLTAGE)" is the phase of the complex frequency domain representation of the known voltage of the AC sinusoidal signal applied to the skin on the human subject's wrist 210, and "Phase(OBTAINED_AC_VOLTAGE)" is the phase of the complex frequency domain representation of the AC voltage signal obtained by the trans-impedance amplifier circuitry 232.

It is noted that the frequency of the phasic component 120b of the exemplary electrodermal signal 120 (see FIG. 1c) is typically less than 0.5 Hz, and that the frequency of the tonic component 120a of the exemplary electrodermal signal 120 is lower than that of the phasic component 120b. Obtaining measures of the magnitude and phase of the human subject's skin impedance ($Z_{SKIN}$) in the complex frequency domain, as in equations (5) and (6) above, therefore allows the frequencies of interest (e.g., the frequencies of the tonic and phasic components 120a, 120b; see FIG. 1c) to be easily separated from undesirable noise frequencies, such as environmental noise frequencies (e.g., 50 or 60 Hz power line noise) and/or noise frequencies from the internal electronics (e.g., greater than 100 Hz) of the EDA monitoring system 200. In this way, the signal-to-noise ratio (SNR) of the EDA monitoring system 200 can be increased over conventional EDA monitoring systems. It is noted that measures of the magnitude and phase of the human subject's skin conductance in the complex frequency domain can be obtained in likewise fashion.

Figure 3:
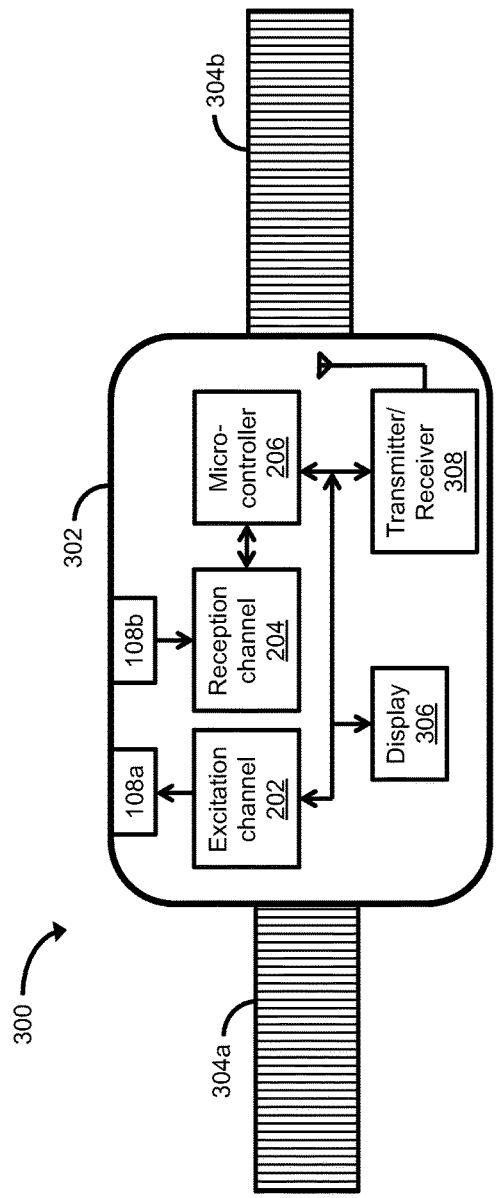
FIG. 3 is a diagram of the system of FIG. 2a implemented in a wristband.

FIG. 3 depicts an illustrative embodiment of the EDA monitoring system 200 of FIG. 2a implemented in a wristband 300. As shown in FIG. 3, the wristband 300 can include a housing 302, a first wrist strap 304a, and a second wrist strap 304b, which, while the wristband 300 is being worn on the wrist 210 of a human subject, can be secured to the first wrist strap 304a by a snap, a buckle, a Velcro® fastener, or any other suitable fastener. The housing 302 is configured to house various components of the EDA monitoring system 200 including the excitation channel 202, the reception channel 204, and the micro-controller 206, as well as a display 306 and a transmitter/receiver 308. In certain embodiments, the housing 302 can be configured to incorporate the first and second dry electrodes 108a, 108b so as to allow the respective dry electrodes 108a, 108b to make proper contact with the skin on the wrist 210 while the wristband 300 is being worn by the human subject. In certain further embodiments, one or both of the wrist straps 304a, 304b can be configured to incorporate one or both of the first and second dry electrodes 108a, 108b, again allowing the respective dry electrodes 108a, 108b to make proper contact with the skin on the wrist 210 while the wristband 300 is being worn by the human subject.

FIG. 4 depicts a typical environment 400 in which the EDA monitoring system 200 implemented in the wristband 300 may be employed. In the typical environment 400, the EDA monitoring system 200 is operative to engage in bidirectional communications over wireless communication paths 410 with a smartphone 402, or any other suitable communications device. The smartphone 402 is operative to engage in bidirectional communications over wireless communication paths 412 with a communications network 404 (e.g., the Internet). The smartphone 402 is further operative, via the communications network 404, to engage in bidirectional communications over wireless communication paths 414 with cloud-based data storage 406, and to engage in bidirectional communications over wireless communication paths 416 with emergency services 408.

The operation of the EDA monitoring system 200 will be further understood with reference to the following illustrative example, as well as FIGS. 2a, 3 and 4. In this illustrative example, the human subject 401 (see FIG. 4) straps the wristband 300 (see FIGS. 3 and 4) with the EDA monitoring system 200 (see FIGS. 2a and 4) implemented therein onto his or her wrist 210, and engages in walking, running, dancing, bicycling, and/or any other suitable activity. While the human subject 401 walks, runs, dances, bicycles, etc., the EDA monitoring system 200 gathers or collects skin impedance or conductance data, as well as environmental data, acceleration data, and/or other physiological data from the human subject 401. For example, the ambient sensor(s) 226 may gather or collect environmental data relating to the external temperature and/or humidity, and the accelerometer 230 may gather or collect acceleration data relating to the human subject's gait or other motion. Further, the physiological sensor(s) 228 may gather or collect physiological data relating to the human subject's wrist-based heart rate and/or heart rate variability, temperature, and/or autonomous nervous system activity. As described herein, the trans-impedance amplifier circuitry 232 can provide an AC voltage signal corresponding to an AC current flowing between the first and second dry electrodes 108a, 108b, and the micro-controller 206 can process and analyze the AC voltage signal to obtain skin impedance or conductance data relating to the human subject's motion and/or environmental, psychological, and/or physiological arousal.

In this illustrative example, the micro-controller 206 can further process and analyze the environmental data, the acceleration data, and/or the physiological data in addition to the skin impedance or conductance data, and store the environmental data, the acceleration data, the physiological data, and/or the skin impedance or conductance data in the memory 244. Moreover, the micro-controller 206 can provide the environmental data, the acceleration data, the physiological data, and/or the skin impedance or conductance data in displayable form to the display 306 and/or the transmitter/receiver 308, which can transmit the various data and associated metrics over the wireless communication paths 410 to the smartphone 402. The smartphone 402 can then transmit, via the communications network 404, some or all of the data/metrics over the wireless communication paths 412, 414 to the cloud-based data storage 406 for subsequent downloading by the human subject 401 and/or a healthcare professional for monitoring and/or tracking purposes. In certain embodiments, based on the environmental data, the acceleration data, the physiological data, and/or the skin impedance or conductance data indicating a potential emergency situation involving the human subject 401, the smartphone 402 can further transmit, via the communications network 404, an alert over the wireless communication paths 412, 416 to the emergency services 408, notifying them of the potential emergency situation. In response, the emergency services 408 can dispatch appropriate emergency personnel and/or equipment to the human subject's geographical location, which may be determined using a global positioning system (GPS) receiver (not shown) included in the smartphone 402 or the EDA monitoring system 200.

An illustrative method of monitoring the EDA in a human subject, using the EDA monitoring system 200, is described below with reference to FIGS. 2a, 2b, 3, 4, and 5. In this illustrative method, the EDA monitoring system 200 is implemented in the wristband 300. As depicted in block 502 (see FIG. 5), the wristband 300 (see FIG. 3) is strapped onto the wrist 210 (see FIG. 2a) of the human subject 401 (see FIG. 4). As depicted in block 504, a square wave signal having a predetermined excitation frequency is generated by the excitation signal source 216. As depicted in block 506, the square wave signal is level-shifted by the level shifter 214, and converted to an AC sinusoidal signal by the low-pass filter 212. As depicted in block 508, the AC sinusoidal signal is provided, via the capacitor 218, to the first dry electrode 108a making contact with a first area of skin on the human subject's wrist 210, thereby causing an AC current to flow from the first area of skin on the human subject's wrist 210, through the stratum corneum of the skin, and ultimately to the second dry electrode 108b making contact with a second area of skin on the human subject's wrist 210. As depicted in block 510, the AC current at the second dry electrode 108b is provided, via the capacitor 220, to the trans-impedance amplifier circuitry 232. As depicted in block 512, the AC current is converted, by the trans-impedance amplifier circuitry 232, to an AC voltage signal.

As depicted in block 518, the AC voltage signal from the trans-impedance amplifier circuitry 232 is selectively provided, by the MUX 236, to the A-to-D converter (ADC) 238 (see FIGS. 2a and 2b), which includes the sample-and-hold circuit 246 and the quantizer/encoder 248. As depicted in block 520, the AC voltage signal from the trans-impedance amplifier circuitry 232 is sampled, by the sample-and-hold circuit 246 (see FIG. 2b), at a predetermined sampling frequency equal to four times (4×) the predetermined excitation frequency in order to obtain a corresponding sampled voltage level sequence. As depicted in block 522, the sampled voltage level sequence corresponding to the AC voltage signal is quantized and encoded by the quantizer/encoder 248 (see FIG. 2b). As depicted in block 524, the quantized and encoded voltage level sequence is provided to the micro-controller 206, which includes the DFT processor 240 and the microprocessor 242. As depicted in block 526, a complex frequency domain representation of the quantized/encoded voltage level sequence is generated by the DFT processor 240. As depicted in block 528, the representation of the quantized/encoded voltage level sequence is processed and analyzed, by the microprocessor 242, in the complex frequency domain in order to obtain a measure of the human subject's skin impedance or skin conductance, each such measure including a magnitude and a phase of the skin impedance or skin conductance in the complex frequency domain.

Having described the above illustrative embodiments of the disclosed EDA monitoring system, other alternative embodiments or variations may be made and/or practiced. For example, it was described herein that the excitation signal source 216 can produce an AC excitation signal having a predetermined excitation frequency of about 100 Hz or 120 Hz. In certain alternative embodiments, the excitation signal source 216 can produce an AC excitation signal having an excitation frequency ranging from about 50 Hz to about 1,000 Hz. It was further described herein that the sample-and-hold circuit 246 within the A-to-D converter 238 can operate at a predetermined sampling frequency of about four times (4×) the predetermined excitation frequency of 100 Hz or 120 Hz (i.e., at a sampling frequency of about 400 Hz or 480 Hz). In certain alternative embodiments, the sample-and-hold circuit 246 can operate at a sampling frequency of about five times (5×), six times (6×), seven times (7×), eight times (8×), or any other suitable number of times the predetermined excitation frequency.

It will be appreciated by those of ordinary skill in the art that modifications to and variations of the above-described systems and methods may be made without departing from the inventive concepts disclosed herein. Accordingly, the invention should not be viewed as limited except as by the scope and spirit of the appended claims.

What is claimed is:

1. A system for monitoring electrodermal activity, comprising:
    a first dry electrode for making contact with a first area of skin;
    a second dry electrode for making contact with a second area of the skin;
    an excitation channel operative to provide an alternating current (AC) excitation signal at a predetermined excitation frequency, thereby causing an AC current to flow between the first dry electrode and the second dry electrode within a stratum corneum of the skin,
        wherein the excitation channel includes an excitation signal source, the excitation signal source being operative to generate the AC excitation signal as a square wave signal;
        wherein the excitation channel further includes a low-pass filter, the low-pass filter operative to convert the square wave signal to an AC sinusoidal signal;
    a reception channel including
        a trans-impedance amplifier configured to convert the AC current to an AC voltage signal and
        an analog-to-digital (A-to-D) converter configured to convert a sampled AC voltage signal to a digitized voltage level sequence; and
    a discrete Fourier transform processor operative to generate a complex frequency domain representation of the digitized voltage level sequence, and to separate noise frequencies from the complex frequency domain representation of the digitized voltage level sequence.

2. The system of claim 1 further comprising:
    integrated circuitry operative to obtain a measure of at least one of skin impedance and skin conductance based on the digitized voltage level sequence.

3. The system of claim 2 wherein the integrated circuitry is further operative to obtain a magnitude of the measure of at least one of the skin impedance and the skin conductance in a complex frequency domain.

4. The system of claim 3 wherein the integrated circuitry is further operative to obtain a phase of the measure of at least one of the skin impedance and the skin conductance in the complex frequency domain.

5. The system of claim 1, wherein the excitation channel further includes a first capacitor, and wherein the low-pass filter is further operative to provide the AC sinusoidal signal to the first dry electrode through the first capacitor.

6. The system of claim 5 wherein the reception channel further includes a second capacitor, and wherein the trans-impedance amplifier is operative to receive the AC current from the second dry electrode through the second capacitor.

7. The system of claim 6 wherein the first capacitor and the second capacitor are operative to provide capacitive isolation for the first area and the second area, respectively, of the skin.

8. The system of claim 1 wherein the predetermined excitation frequency is one of about 100 Hertz (Hz) and about 120 Hz.

9. A system for monitoring electrodermal activity, comprising:
   a first dry electrode for making contact with a first area of skin;
   a second dry electrode for making contact with a second area of skin;
   an excitation signal source operative to generate a square wave signal at a predetermined excitation frequency;
   a level shifter operative to level-shift the square wave signal;
   a low-pass filter operative to convert the level-shifted square wave signal to an alternating current (AC) sinusoidal signal, and to apply the AC sinusoidal signal to a first capacitor connected to the first dry electrode, thereby causing an AC current to flow between the first dry electrode and the second dry electrode within the stratum corneum of the skin;
   a trans-impedance amplifier operative to receive the AC current through a second capacitor connected to the second dry electrode and to convert the AC current to an AC voltage signal;
   an analog-to-digital (A-to-D) converter having a sample-and-hold circuit configured to sample the AC voltage signal and generate a sampled AC voltage signal, wherein the A-to-D converter is configured to convert the sampled AC voltage signal to a digitized voltage level sequence; and
   integrated circuitry operative to obtain a measure of at least one of skin impedance and skin conductance based on the digitized voltage level sequence, wherein the integrated circuitry is further operative to separate noise frequencies from the digitized voltage level sequence.

10. The system of claim 9 wherein the integrated circuitry is further operative to obtain a magnitude of the measure of at least one of the skin impedance and the skin conductance in a complex frequency domain.

11. The system of claim 10 wherein the integrated circuitry is further operative to obtain a phase of the measure of at least one of the skin impedance and the skin conductance in the complex frequency domain.

12. The system of claim 9 wherein the predetermined excitation frequency is one of about 100 Hertz (Hz) and about 120 Hz.

13. The system of claim 9, wherein the sample-and-hold circuit is configured to sample the AC voltage signal at a sampling frequency of four times (4×) the predetermined excitation frequency.

14. The system of claim 9, further comprising a discrete Fourier transform (DFT) processor operative to generate a complex frequency domain representation of the digitized voltage level sequence.

15. The system of claim 9, wherein the AC current between the first dry electrode and the second dry electrode flows through a stratum corneum of the skin.

16. The system of claim 1, wherein the A-to-D converter includes a sample-and-hold circuit configured to sample the AC voltage signal at a sampling frequency and generate the sampled AC voltage signal.

17. The system of claim 16, wherein the sampling frequency is about four times (4×) the predetermined excitation frequency.

18. A apparatus for monitoring electrodermal activity, comprising:
   a first dry electrode for making contact with a first area of skin;
   a second dry electrode for making contact with a second area of the skin;
   an excitation channel operative to provide an alternating current (AC) excitation signal at a predetermined excitation frequency, thereby causing an AC current to flow between the first dry electrode and the second dry electrode within the stratum corneum of the skin;
   an amplifier configured to convert the AC current to an AC voltage signal;
   an analog-to-digital (A-to-D) converter having a sample-and-hold circuit configured to sample the AC voltage signal, wherein the A-to-D converter is configured to convert the sampled AC voltage signal to a digitized voltage level sequence; and
   a discrete Fourier transform processor operative to generate a complex frequency domain representation of the digitized voltage level sequence, and to separate noise frequencies from the complex frequency domain representation of the digitized voltage level sequence.

19. The system of claim 1, wherein the noise frequencies include at least one of environmental noise frequencies, 50 Hz power line noise, and 60 Hz power line noise.

20. The apparatus of claim 18, further comprising integrated circuitry operative to obtain a measure of at least one of skin impedance and skin conductance based on the digitized voltage level sequence.

21. The system of claim 20, wherein the integrated circuitry is further operative to obtain a magnitude of the measure of at least one of the skin impedance and the skin conductance in a complex frequency domain.

22. The system of claim 21, wherein the integrated circuitry is further operative to obtain a phase of the measure of at least one of the skin impedance and the skin conductance in the complex frequency domain.

* * * * *